United States Patent [19]

Roberts

[11] 4,034,419
[45] July 12, 1977

[54] FULL EXTENSION LOCK FOR PROSTHETIC KNEE JOINT

[75] Inventor: Roy Daniel Roberts, San Jose, Calif.

[73] Assignee: Hosmer/Dorrance Corporation, Campbell, Calif.

[21] Appl. No.: 608,389

[22] Filed: Aug. 27, 1975

[51] Int. Cl.² .................................. A61F 1/04
[52] U.S. Cl. ............................................... 3/26
[58] Field of Search .......................... 3/22–27; 403/322, 325, 330; 292/166, 153, 171, 181

[56] References Cited

U.S. PATENT DOCUMENTS

| | | | |
|---|---|---|---|
| 1,313,599 | 8/1919 | Webb | 3/27 |
| 1,685,290 | 9/1928 | Neumann | 3/23 |
| 2,573,347 | 10/1951 | Mazzola | 3/24 |
| 3,806,958 | 4/1974 | Gusev | 3/22 |

*Primary Examiner*—Louis G. Mancene
*Assistant Examiner*—Wenceslao J. Contreras
*Attorney, Agent, or Firm*—Harris Zimmerman

[57] ABSTRACT

A device for locking a prosthetic knee joint in full extension includes a housing having a friction shoe adjustably impinging on a standard extension limit link extending through the housing. A latch lever is pivotally secured in the housing and is spring biased toward the extension limit link, with a detent adapted and positioned for engaging the end of the link only during full extension. A release cable or rod extending through the housing is adapted to pull against the spring bias to release the link from the detent, and to reset the latch lever during genuflection to once again engage the link when full extension is again attained. The release rod is manually controlled by an over-center cam toggle, or by a flexible cable extending upward toward the hip and controlled by a similar toggle.

12 Claims, 8 Drawing Figures

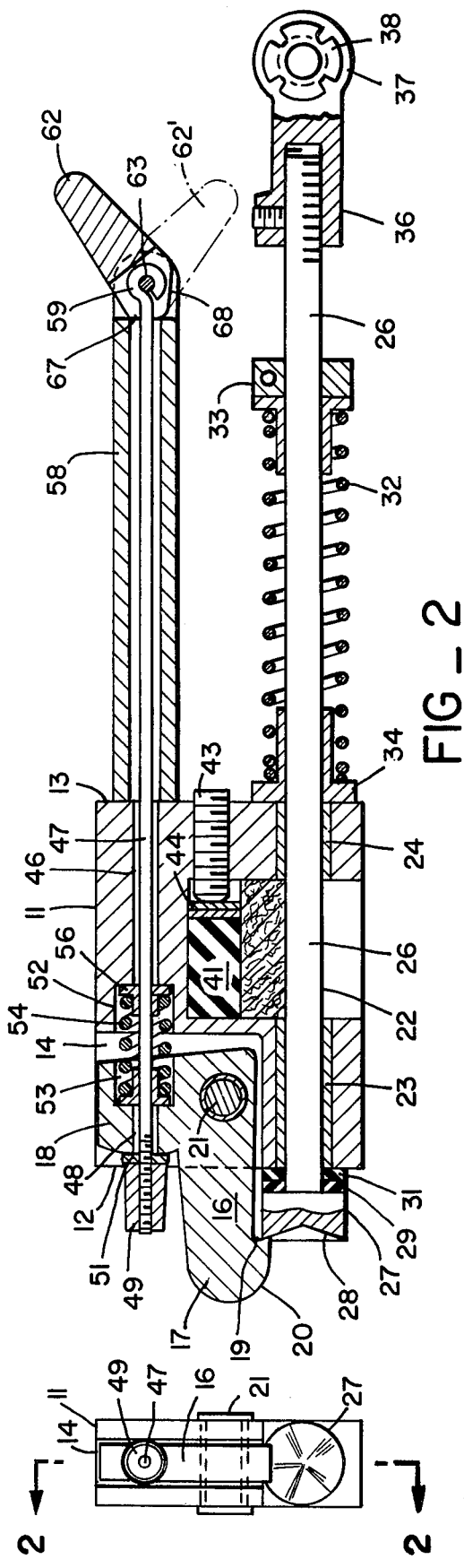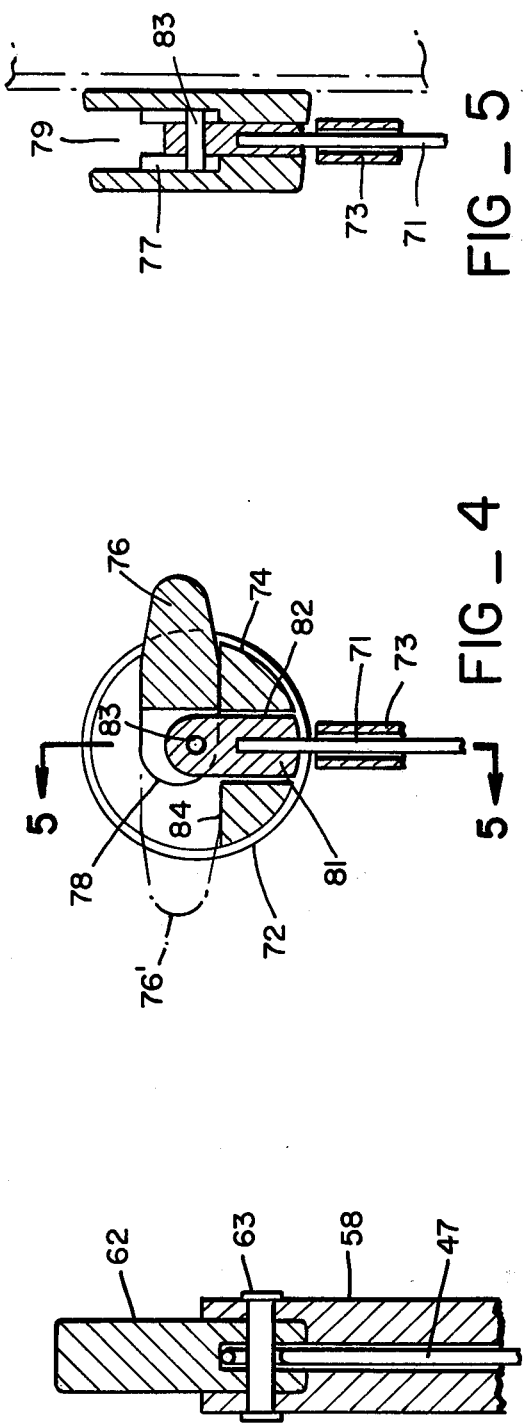

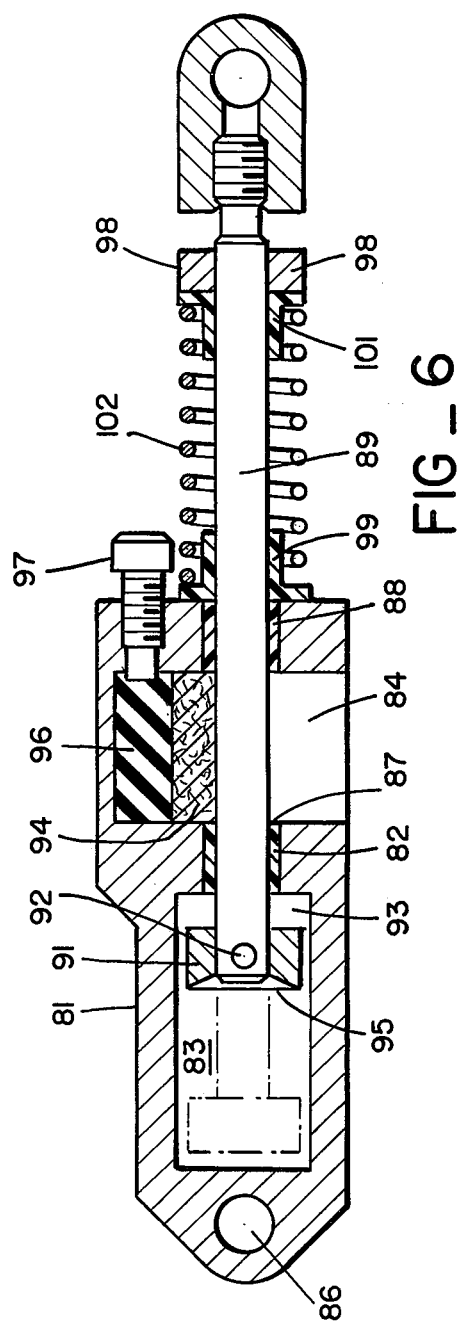
FIG_6
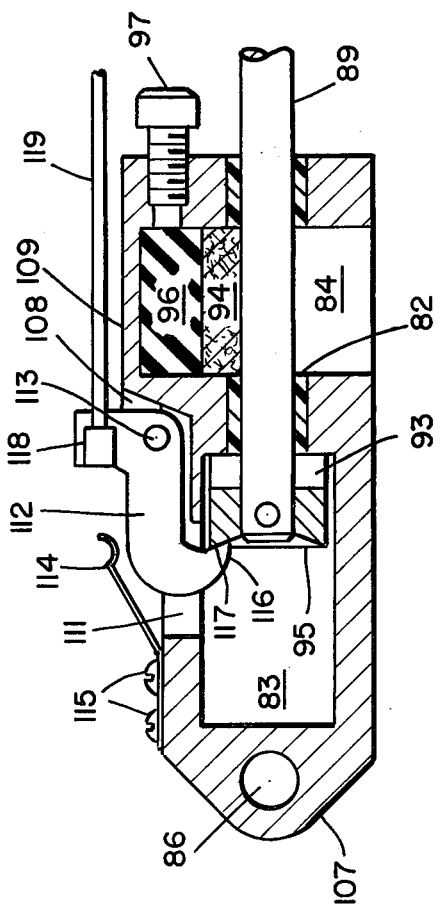
FIG_7
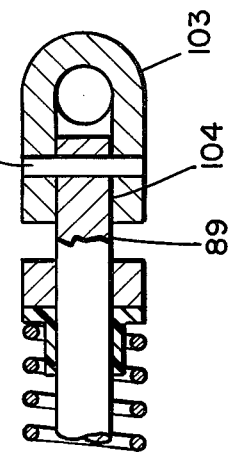
FIG_8

FULL EXTENSION LOCK FOR PROSTHETIC KNEE JOINT

BACKGROUND OF THE INVENTION

In the prosthetic art it is well-known to provide a leg prosthesis having a single-axis joint which is lockable in the fully extended leg position to prevent flexure during walking or standing. In the event that the wearer desires to bend the leg to sit down or the like, the joint must be manually unlocked. Similarly, should the wearer wish to rise from a sitting position, the knee joint must be locked immediately after rising, as soon as the leg is fully extended. These locking and unlocking procedures usually require the wearer to bend from the waist and manually actuate a lever or toggle in the hinge lock. Such a task is awkward and is a persistent nuisance. Although more automatic knee joints are available, their cost is prohibitive for many amputees. Thus an economical device for modifying the simple single-axis knee joint to provide easier locking and unlocking thereof is highly desirable.

SUMMARY OF THE INVENTION

The present invention provides a locking device adapted to be incorporated and substituted on single axis knee joint prostheses and the like. The locking device releasably secures the leg in the fully extended position, and provides a manual toggle actuator on the leg remote from the device and within easy reach of the wearer.

Generally speaking, the invention provides a housing secured to the leg below the knee, through which an extension link slidably extends. The upper end of the link is joined to a pivot pin provided on the knee portion of the leg, and the link is dimensioned so that the lower end thereof abuts the upper end of the inside of the housing coincident with full extension of the knee joint. The housing is provided with a friction shoe assembly well-known in the art, and the link is provided with a compression spring to bias the link to fully extend the knee joint.

At the lower end of the housing is disposed a pivoting latch lever which is spring biased so that a detent extending therefrom is urged toward the extension link adjacent thereto. The detent is adapted to engage the lower end of the link only from below, to prevent the link from translating downward. Thus the detent locks the link at the fully extended position.

The lower end of the latch lever is joined to a release member which may be put under tension to cause the latch lever to pivot and disengage the extension link. The release member (a cable or rod) extends upward to a toggle actuator disposed on the shank of the leg within easy reach of the wearer. The toggle employs an over-center pivotting cam to tension or slacken the release member.

The wearer may employ the toggle to release the detent just prior to sitting, or the like. The toggle may also be used to slacken the release member prior to the wearer's standing, so that as the wearer stands and the leg prothesis extends fully, the link will fully translate and be automatically locked in that disposition by the detent on the spring-biased latch lever.

THE DRAWING

FIG. 1 is an end view of the housing of the present invention.

FIG. 2 is a cross-sectional side elevation of the housing of the present invention, taken along line 2—2 of FIG. 1.

FIG. 3 is a sectional side elevation of the toggle assembly of the present invention.

FIG. 4 is a sectional front elevation of an alternative embodiment of the toggle assembly of the present invention.

FIG. 5 is a sectional side elevation of the alternative toggle assembly, taken along line 5—5 of FIG. 4.

FIG. 6 is a sectional side elevation of a further embodiment of the present invention.

FIG. 7 is a sectional side elevation of another embodiment of the present invention, showing the housing thereof.

FIG. 8 is a sectional side elevation of another embodiment of the present invention.

DESCRIPTION OF THE PREFERRED EMBODIMENT

With reference to FIGS. 1 and 2, the present invention includes a generally rectangular housing 11 having a lower end 12 and an upper end 13. The lower end 12 is provided with a rectangular slot 14 extending therein, in which is disposed a latch lever 16. The latch lever includes two normally extending legs 18 and 17, the latter being provided with a hooked detent 19 at the distal end thereof. A pivot pin 21 within a bushing extends through the housing, the slot, and the latch lever, permitting the latter to pivot freely. The housing is secured to the leg prosthesis below the knee by any means known in the art, such as rivets, screws, a bracket, or the like.

The housing is provided with a passage 22 extending therethrough, and includes bushings 23 and 24 which permit an extension link 26 to slide freely therethrough. The lower end of the link 26 terminates in a head 27 which includes a shallow depression 28 in the end thereof. The depression permits the detent 19 to easily engage and retain the head of the link. A pair of felt cushioning washers 29 and 31 are secured about the link and joined to the lower end of the housing, limiting the upward translation of the link, and act a a noise suppression at full extension.

Medially disposed about the extension link 26 is a helical compression spring 32, situated between a collar 33 secured on the link, and a collar 34 through which the link translates. The spring 32 biases the link upward toward the full extension position. The upper end of the link is threaded to receive thereon a rod end fitting 36. The fitting is provided with a hole 37, lined with a bushing 38 and adapted to receive a standard pivot pin typically extending from the shank portion of a leg prosthesis. The extension link is dimensioned so that the lower end thereof abuts the housing coincident with full extension of the knee joint prosthesis.

Within the housing is disposed an elastic rubber pressure pad 41, which is adjacent to a friction shoe 42. The shoe is provided with a groove through which the extension link translates. A set screw 43 is threadedly received in the upper end of the housing, its end abutting a pressure plate 44 which impinges on the pressure pad 41. The set screw is adjusted to compress the pressure pad axially, causing it to elastically expand laterally and impinge on the friction shoe. In this manner the frictional relationship between the friction shoe and the extension link is adjusted.

A second passageway 46 extends through the housing, parallel to the passageway 22, from the upper end 13 to the slot 14. In this passageway is disposed a release rod 47, freely translating therein. The leg 18 of the latch lever is provided with a hole 48 therethrough, coaxial with the passageway 46, through which the rod 47 also extends. The lower end of the rod 47 is threaded to receive a knurled adjustment nut 49, which is spaced from the leg 18 by a washer 51.

The passageway 46 and hole 48 are provided with opposed counterbores 52 and 53, respectively. Disposed therein is a helical compression spring 54, supported on opposed collars 56 which are freely received on the rod 47. The spring 54 biases the latch lever with a counterclockwise force (as seen in FIG. 2), urging the detent 19 toward the extension link. Thus the detent, if unchecked, will normally engage the head of the link at full extension, thereby locking the fully extended knee joint.

The release rod 47 extends upward through a hollow strut 58, and terminates in an eye 59 at the upper end. The eye is received in the clevis end 61 of a toggle handle 62. A pivot pin 63 with its ends secured in the strut wall extends through aligned holes 64 in the clevis and the eye (FIGS. 2 and 3). At the end of the clevis is disposed a cam surface which impinges on the end of the strut. The portion 67 of the cam surface is spaced further from the pivot pin than the portion 68. Thus the angular orientation of the handle 62 can determine the translation and disposition of the release rod 47, according to which face of the cam surface is presented to impinge on the strut.

With the handle disposition shown in FIG. 2 in solid line, the surface 67 contacts the strut, urging the release rod upward and rotating the latch lever clockwise. This rotation causes the detent to disengage the head of the extension link, so that no locking action is provided. In the disposition shown in phantom at 62', the surface 68 is presented to the strut, and the rod 47 is allowed to translate slightly downward so that the latch lever may rotate counterclockwise to engagement position.

In this disposition (62'), the detent will engage the head 27 of the link if the link (and leg) is fully extended. If the leg is genuflected, no locking action is obtainable. However, as the leg is fully extended the oblique surface 20 of the detent will ride over the head as it translates upward. When full extension is reached, the detent will lock automatically.

Thus the wearer of the present invention may, while sitting with the knee genuflected, set the handle to the position of 62'. Upon rising, as the leg fully extends due to the action of spring 32, the leg will lock automatically in the extended position for walking or standing.

In an alternative embodimdent of the present invention, the latch lever is controlled by a flexible cable instead of the rigid rod 47. The cable 71 is joined to the latch lever in the same way, and its extends upward through a guide 73 to a toggle assembly 72 (FIGS. 4 and 5). The assembly includes a housing 74 secured to the prosthesis and having a slot 79 in the upper end thereof, in which is disposed a handle 76. The handle has a cleavis end 77 with an arcuate edge 78.

The upper end of the cable is soldered or otherwise secured in a fitting 81 which extends through a hole 82 in the housing to a medial situation between the tines of the clevis 77. A pin 83 extends pivotally through the tines and the fitting, joining them together. The pin is located eccentrically with respect to the center of arc of edge 78 to provide an over-center cam action on the surface 84 of the slot 79. The disposition of handle 76 shown in solid line in FIG. 4 releases the cable to provide automatic locking, as described previously. The disposition depicted in phantom line at 76' tensions the cable to release and disable the locking action.

A further embodiment of the present invention, as shown in FIG. 6, generally comprises a friction unit for a prosthetic knee joint to which a locking unit may be added as desired. It includes a generally rectangular housing 81 having a centrally disposed passageway 82 extending therein. Within the housing is a rectangular hole 83 communicating with the passageway 82. Another hole 84 extends into the housing transversely to the hole 83 and the passageway 82. The housing includes a mounting hole 86, and is preferably fabricated of extruded aluminum for durability and light weight.

Within the passageway 82 are disposed sleeves 87 and 88 which slidably receive therethrough a rod 89. One end of the rod extends into the hole 83, and includes a rectangular collar 91 secured thereto by a pin 92 passing through the collar and rod. Joined to one end of the collar is a resilient cushion 93 which reduces noise and impact forces due to the collar striking the housing portion adjacent to sleeve 87. The other end of the collar includes a shallow depression 95. A friction shoe 94 is received in the hole 84 and positioned to impinge on the rod 89. An elastic pressure pad 96 impinges on the friction pad with a force selectively varied by an adjusting screw 97, received in the housing, which compresses the pressure pad. The shoe and adjusting screw function as described in the foregoing.

Secured to a distal end portion of the rod 89 is a collar 98, which may be either threadedly engaged on the rod or pinned in placed in the same fashion as the collar 91. A pair of bushings 99 and 101 are slidably secured on the rod, the former abutting the housing and the latter abutting the collar 98. Disposed about the rod and received between the bushings is a helical compression spring 102 which biases the rod to extend out of the housing. The distal end of the rod is threaded, and receives an end fitting 103 which joins the device to a prosthetic leg.

Alternatively, as shown in FIG. 8, the end of the rod 89, is not threaded, and is received in a smooth hole 104 in the fitting 103. The end fitting and rod are provided with aligned holes extending diametrically therethrough, and a pin 106 is press fit through the holes to join the two members. With this construction the rod is not threaded, permitting the use of materials which, being notch-sensitive, would be inappropriate for a threaded member. For example, stainless steel may be used as the rod material, as it may be heat-treated to a relatively high hardness, and it needs not be plated to avoid corrosion. It should be noted, also, that the rectangular collar 91 translating in the rectangular hole 83 prevents any rotation of the rod 89.

A singular advantage of the friction unit shown in FIG. 6 is that it may be easily converted to a locking friction unit. As shown in FIG. 7, the housing 81 is replaced by a new housing 107. The housing 107 has similar holes 82, 83, and 84, and sleeves 87 and 88 for receiving the rod 89. Also, the adjustable friction assembly 94, 96, and 97 is the same as in the previous embodiment. A slot 108 is disposed in the upper surface 109 of the housing, and includes a portion 111 which communicates with the hole 83. Disposed in the slot is a latch lever 112, pivotally secured therein by a pin 113 which extends therethrough and through the opposed sides of the slot.

A leaf spring 114 is secured to the surface 109 of the housing by screws 115 or the like, and is disposed to impinge on the latch lever and resiliently urge it into the hole 83. The latch lever includes a detent 116 extending into the hole 83 and having a detent surface 117 extending at approximately the same angle as the surface 95 of the collar 91. The exterior end 117 of the latch lever includes a counterbored hole 118 therethrough for securing a lanyard or cable 119. The latch lever 112 and lanyard function in the same manner as the latch 16 and rod 47 of the previous embodiment.

It should be noted that the angularity of the bearing 95 and 117 provide a self-locking engagement. The resilience of the cushion 93 serves to maintain such engagement, as well as reduce noise and shock. Urging the rod 89 toward the housing will only increase the force required to rotate the locking link to the release position. Also, the broad engagement surfaces of the collar and link permit the use of softer material, such as extruded aluminum, in fabricating the latch lever.

I claim:

1. A device for locking in fixed relationship two hinged members, comprising;
    a housing secured to one of the hinged members,
    an extension link joined at one end to the other hinged member, said extension link translating and slidably extending through a passageway in said housing,
    latch means secured to said housing for releasably retaining the other end of said extension link,
    release means secured in said housing for releasing said latch means, and
    actuator means remote from said housing for controlling said release means.

2. The device of claim 1, wherein said other end of said extension link includes an enlarged head.

3. The device of claim 1, wherein said latch means includes a latch lever pivotally secured to said housing, said latch lever including a detent extending therefrom for unidirectionally engaging said other end of said extension link.

4. The device of claim 3, including resilient means for biasing said latch lever to engage said detent with said other end of said extension link.

5. The device of claim 3, wherein said release means includes a tension member extending through said housing and joined at one end to said actuator means, and at the other end to the lever end of said latch lever.

6. The device of claim 5, including adjustment nut means joined to said other end of said tension member for selectively spacing said lever end of said latch lever and said other end of said tension member.

7. The device of claim 3, wherein said other end of said extension link is disposed to receive said detent at full extension of said hinged members.

8. The device of claim 1, further including friction means for applying frictional impedance to said translating extension link.

9. The device of claim 1, wherein said actuator means includes a toggle handle having an external cam surface.

10. The device of claim 9, wherein said release means includes a tension member extending from said latch means to said actuator means.

11. The device of claim 10, wherein said toggle handle includes a clevis, and said tension member is pivotally secured between the tines of said clevis.

12. The device of claim 1, further including spring means secured to said extension link for axially biasing said extension link toward said one end thereof.

* * * * *